US010209266B2

(12) United States Patent
Haustein et al.

(10) Patent No.: US 10,209,266 B2
(45) Date of Patent: *Feb. 19, 2019

(54) BIOSAMPLE PLATE WITH DATA STORAGE AND WIRELESS COMMUNICATIONS

(71) Applicant: International Business Machines Corporation, Armonk, NY (US)

(72) Inventors: Nils Haustein, Soergenloch (DE); Thorsten Krause, Kressbronn (DE); Anna W. Topol, Clifton Park, NY (US); Daniel J. Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 507 days.

This patent is subject to a terminal disclaimer.

(21) Appl. No.: 14/879,032

(22) Filed: Oct. 8, 2015

(65) Prior Publication Data

US 2016/0033499 A1   Feb. 4, 2016

Related U.S. Application Data

(62) Division of application No. 13/151,265, filed on Jun. 1, 2011, now Pat. No. 9,417,237.

(51) Int. Cl.
*B01L 3/00*   (2006.01)
*G01N 35/00*   (2006.01)
(Continued)

(52) U.S. Cl.
CPC ......... *G01N 35/00732* (2013.01); *B01L 3/50* (2013.01); *B01L 3/508* (2013.01);
(Continued)

(58) Field of Classification Search
CPC ......... B01L 2300/022; B01L 2300/023; B01L 2300/024; B01L 2300/0809;
(Continued)

(56) References Cited

U.S. PATENT DOCUMENTS 3,859,624 A   1/1975   Kriofsky et al.
4,650,981 A   3/1987   Foletta
(Continued)

OTHER PUBLICATIONS

Non-Final Office Action from U.S. Appl. No. 13/151,265, dated Nov. 2, 2015.
(Continued)

*Primary Examiner* — Erik B Crawford
(74) *Attorney, Agent, or Firm* — Zilka-Kotab, P.C.

(57) ABSTRACT

Embodiments of the disclosure relate to a biosample plate that includes a memory component for storing biosample identification and analysis data, and a wireless communication interface for transferring the data to and from the biosample plate. In one embodiment, the biosample plate comprises a base for receiving a biosample, a memory component coupled to the base for storing identification and analysis information related to the biosample, and a wireless communication interface coupled to the memory component for transferring the information to and from the memory component. The wireless communication interface may include an optical device.

19 Claims, 7 Drawing Sheets (51) Int. Cl.
  *G01N 33/487* (2006.01)
  *G01N 33/553* (2006.01)
  *G06F 3/06* (2006.01)

(52) U.S. Cl.
  CPC ............. *B01L 3/5085* (2013.01); *B01L 3/545* (2013.01); *G01N 33/48792* (2013.01); *G01N 33/553* (2013.01); *G01N 35/00029* (2013.01); *G01N 35/00871* (2013.01); *G06F 3/061* (2013.01); *G06F 3/0661* (2013.01); *G06F 3/0676* (2013.01); *B01L 2200/025* (2013.01); *B01L 2200/10* (2013.01); *B01L 2300/021* (2013.01); *B01L 2300/023* (2013.01); *B01L 2300/024* (2013.01); *B01L 2300/0809* (2013.01); *G01N 2035/00019* (2013.01); *G01N 2035/00089* (2013.01); *G01N 2035/00099* (2013.01); *G01N 2035/00841* (2013.01)

(58) Field of Classification Search
  CPC ..... B01L 2300/0816; B01L 2300/0851; B01L 3/50; B01L 3/508; G01N 35/00019; G01N 35/00029; G01N 35/00089; G01N 35/00099; G01N 35/00732; G01N 35/00871; G01N 33/48792
  See application file for complete search history.

(56) References Cited

U.S. PATENT DOCUMENTS

| | | | |
|---|---|---|---|
| 4,758,836 | A | 7/1988 | Scuilli |
| 4,941,201 | A | 7/1990 | Davis |
| 5,005,096 | A | 4/1991 | Krounbi et al. |
| 5,206,590 | A | 4/1993 | Dieny et al. |
| 5,465,185 | A | 11/1995 | Heim et al. |
| 5,764,567 | A | 6/1998 | Parkin |
| 6,329,139 | B1 | 12/2001 | Nova et al. |
| 6,332,363 | B1 | 12/2001 | Molloy et al. |
| 6,699,437 | B1 | 3/2004 | Astle |
| 7,118,708 | B2 | 10/2006 | Mordekhay |
| 7,375,910 | B2 | 5/2008 | Bates et al. |
| 7,382,258 | B2 | 6/2008 | Oldham et al. |
| 7,660,063 | B2 | 2/2010 | Bates et al. |
| 7,702,164 | B2 | 4/2010 | Bates et al. |
| 7,724,631 | B2 | 5/2010 | Bates et al. |
| 9,034,660 | B2 | 5/2015 | Boday et al. |
| 9,417,237 | B2 | 8/2016 | Haustein et al. |
| 2002/0197417 | A1 | 12/2002 | Nakamura et al. |
| 2004/0092025 | A1 | 5/2004 | Mordekhay |
| 2006/0202269 | A1 | 9/2006 | Suzuki et al. |
| 2006/0223078 | A1 | 10/2006 | Changming et al. |
| 2007/0189921 | A1 | 8/2007 | Duong et al. |
| 2007/0285225 | A1 | 12/2007 | Koyama et al. |
| 2008/0067079 | A1 | 3/2008 | Takahashi et al. |
| 2009/0066934 | A1 | 3/2009 | Gao et al. |
| 2009/0117011 | A1 | 5/2009 | Morrison |
| 2010/0134286 | A1 | 6/2010 | Potyrailo et al. |
| 2010/0285082 | A1* | 11/2010 | Fernandez ........... A61B 5/0215 424/422 |
| 2011/0076670 | A1 | 3/2011 | Boday et al. |
| 2011/0101996 | A1 | 5/2011 | Potyrailo |
| 2012/0071342 | A1 | 3/2012 | Lochhead et al. |
| 2012/0309111 | A1 | 12/2012 | Haustein et al. |
| 2016/0033542 | A1 | 2/2016 | Haustein et al. |
| 2016/0327584 | A1 | 11/2016 | Haustein et al. |

OTHER PUBLICATIONS

Das et al., "Biocompatibility of diamond-like nanocomposite thin films," J. Mater. Sci.: Mater. Med., vol. 18, Mar. 2007, pp. 493-500.
Philips Semiconductors, "MALT Reader Data Specification," Philips Semiconductors, Aug. 1998, pp. 1-24.
Election/Restriction Requirement from U.S. Appl. No. 13/151,265, dated Jan. 7, 2013.
Non-Final Office Action from U.S. Appl. No. 13/151,265, dated May 6, 2013.
Final Office Action from U.S. Appl. No. 13/151,265, dated Nov. 5, 2013.
Non-Final Office Action from U.S. Appl. No. 13/151,265, dated Nov. 6, 2014.
Final Office Action from U.S. Appl. No. 13/151,265, dated May 7, 2015.
Haustein et al., U.S. Appl. No. 13/151,265, filed Jun. 1, 2011.
Boday et al., U.S. Appl. No. 12/888,388, filed Sep. 22, 2010.
Notice of Allowance from U.S. Appl. No. 13/151265, dated May 10, 2016.
Haustein et al., U.S. Appl. No. 15/214,301, filed Jul. 19, 2016.
Haustein et al., U.S. Appl. No. 14/879,056, filed Oct. 8, 2015.
Restriction Requirement from U.S. Appl. No. 14/879,056, dated Feb. 9, 2018.
Non-Final Office Action from U.S. Appl. No. 14/879,056, dated Jun. 11, 2018.
Restriction Requirement from U.S. Appl. No. 15/214,301, dated Jul. 13, 2018.
Non-Final Office Action from U.S. Appl. No. 15/214,301, dated Oct. 1, 2018.
Notice of Allowance from U.S. Appl. No. 14/879,056, dated Dec. 3, 2018.

* cited by examiner

BIOSAMPLE PLATE WITH DATA STORAGE AND WIRELESS COMMUNICATIONS

BACKGROUND

The invention relates to analytical devices, and more particularly, to a biosample plate with a memory module for storing biosample identification and analysis data, and a wireless communication interface for transferring data to and from the biosample plate.

Samples of biological matters are commonly used for detecting the presence of bacteria, viruses, cancer, and other substances of interest. The biological samples are typically placed on biosample plates to be analyzed by a biological detection instrument. The biological detection instrument may record analysis results on a data storage medium such as computer memories, disk drives, magnetic tapes, and CDs. The biological detection instrument may need some means to correlate a biosample with its analysis results.

For a large number of biosamples and biosample plates, the correlation between the biosamples, biosample plates, and data resulting from various types of analysis can become a complex task. It is desirable to exploit the use of data storage and wireless communication technologies to facilitate the correlation of biosample plates, biosamples, and their analysis data.

SUMMARY

The disclosure relates to a biosample plate that includes a memory component for storing biosample identification and analysis data, and a wireless communication interface for transferring the data to and from the biosample plate. In one embodiment, the biosample plate comprises a base for receiving a biosample, a memory component coupled to the base for storing identification and analysis information related to the biosample, and a wireless communication interface coupled to the memory component for transferring the information to and from the memory component. The wireless communication interface may include an optical device.

In another embodiment, a method comprises analyzing a biosample attached to a base, wherein the base includes a memory component for storing information from the analysis of the biosample, and transferring information to and from the memory component through a wireless communication interface coupled to the memory component. The wireless communication interface may include an optical device.

In still another embodiment, a computer program product comprises a computer readable storage medium having program instructions stored thereon, including first program instructions executable by a computer to cause the computer to analyze a biosample attached to a base, the base comprises a memory component. Second program instruction are executable by the computer to cause the computer to store information from the biosample analysis in the memory component through an optical communication interface coupled to the memory component.

The details of the preferred embodiments of the disclosure, both as to its structure and operation, are described below in the Detailed Description section in reference to the accompanying drawings. The Brief Summary is intended to identify key features of the claimed subject matter, but it is not intended to be used to limit the scope of the claimed subject matter.

DETAILED DESCRIPTION

Embodiments of the disclosure relate to a biosample plate for holding a sample of a matter to be analyzed, such as a biological sample in a bio-detection process. The biosample plate includes a memory component for storing information related to the biosample plate and biosample analysis, and a wireless communication interface for transferring information to and from the biosample plate. The biosample plate, as disclosed, allows the biosample plate identification information and analysis data to conveniently remain with the respective biosample both when the biosample plate is in use and when it is in storage. The disclosed biosample plate thus facilitates the correlation between a large number of analyzed biosample plates and their analysis data and allows data related to the biosample plate to be stored with the biosample plate and readily available to an analytical system or data storage system when needed.

Exemplary embodiments of the invention further include a wireless communication interface, such as a radio antenna, coupled to the data storage element for wireless transfer of data between the biosample plate and an analytical system or a data storage system. The wireless communication interface enables high-speed writing and reading of data on the biosample plate, for example, using a computer tape drive system. Further details on the wireless communication interface and memory component are described below with reference to FIGS. 2-5.

Figure 1:
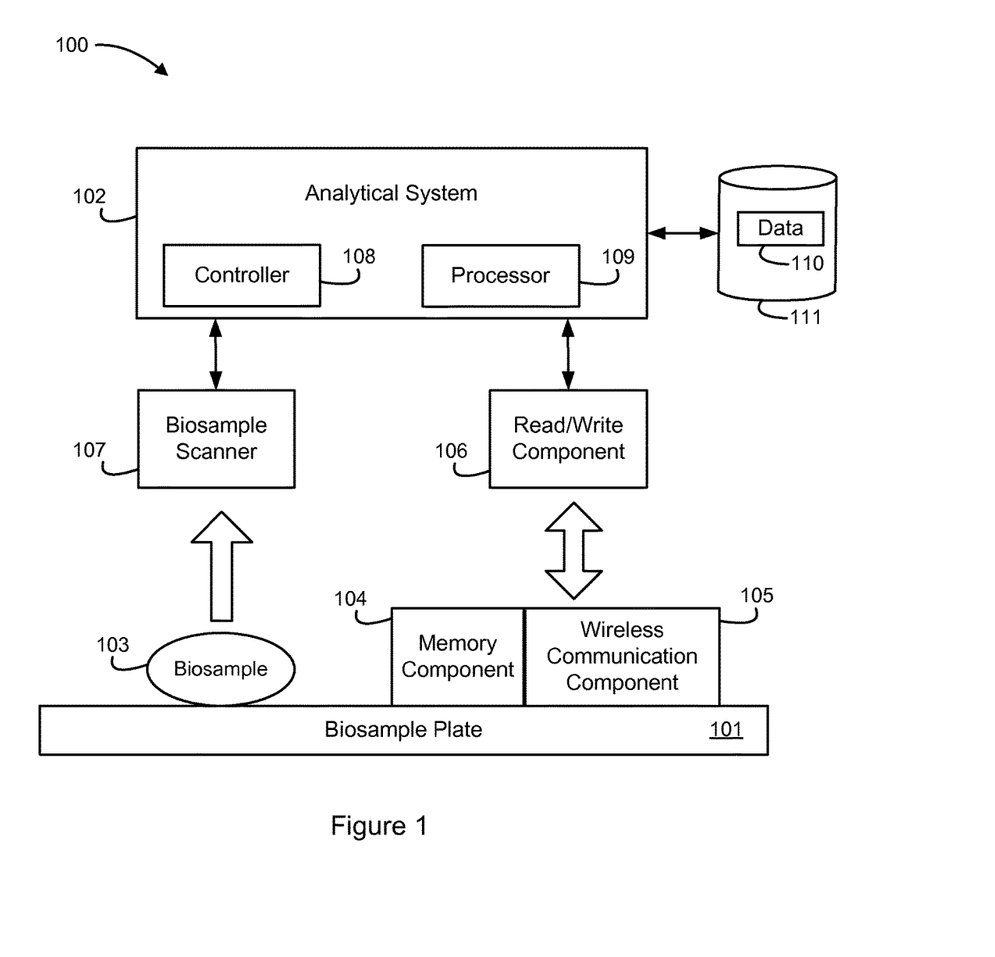
FIG. 1 illustrates a biosample plate with a memory component and a wireless communication interface for use with an analytical system or a data storage system, in accordance with an embodiment of the invention.

Referring to the drawings and in particular to FIG. 1, there is illustrated an exemplary embodiment of a biosample plate 101 with a data storage means and a wireless communication interface for use with an analytical system or data storage system 102. The biosample plate 101 may be fabricated of glass, Pyrex™, or ceramic material and capable of receiving a biosample 103 such as blood, bodily fluids, or other biological matters. The biosample plate 101 includes a memory component 104 for storing plate identification and biological analysis data related to the biosample 103 and biosample plate 101. The memory component 104 may be a nonvolatile memory such as an electrically-erasable programmable read-only memory (EEPROM), a phase-change memory, a flash memory, a NOR memory, or a NAND memory.

The biosample plate 101 may include a wireless communication interface 105 that is in electrical communication with the memory component 104 and capable of wireless transmission of data to and from a read/write component or transceiver 106. Although FIG. 1 illustrates the read/write component 106 as a separate component that is coupled to the analytical system or data storage system 102, the read/write component 106 may be part of the analytical system or data storage system 102.

In one embodiment, the analytical system 102 includes a digital read-write component 106 for sending data to and receiving data from the memory component 104 of the biosample plate 101 via the wireless communication interface 105. The transmitted data may include biosample plate identification information and analysis data of the biosamples on the biosample plate 101. Wireless communication between the digital read-write component 106 and wireless communication interface 105 may be in the form of radio signals, optical signals, or electromagnetic signals. The analytical system 102 may comprise a processor 109 for processing input/output data.

The wireless communication interface 105 may comprise a radio antenna for communicating with the read/write component 106 by radio signals. Data transfer between wireless communication components, such as the wireless communication interface 105 and read/write component 106, using radio signals is described, for example, in U.S. Pat. No. 7,375,910 and the MALT Reader Data Specification published by Philips Semiconductors, August 1998, which are herein incorporated by reference in their entirety.

Alternatively, the wireless communication interface 105 may be an optical interface for communicating with the transceiver 106 by optical signals, such as holographics and lasers. Data transfer using holographics and lasers is described, for example, in U.S. Pat. Nos. 7,702,164 and 7,724,631, which are herein incorporated by reference in their entirety.

In another embodiment, the wireless communication interface 105 may be an electromagnetic interface for communicating with the read/write component 106 by magnetic signals, for example, using magneto-resistive read/write technology. Data transfer between the wireless communication interface 105 and transceiver 106 using magneto-resistive read/write technology is described, for example, in U.S. Pat. No. 7,660,063, which is herein incorporated by reference in its entirety.

The analytical system 102 may be connected to or include a scanner 107 for scanning the biosample 103 to detect the presence of certain micro-organisms or substances in the biosample 103 using, for example, a target organism or substance matching process. In one embodiment, the scanner 107 may comprise magneto-resistive read-sensors commonly used in computer disk and tape drive systems. Examples of magneto-resistive read-sensors include anisotropic magneto-resistive (AMR), giant magneto-resistive (GMR), and tunnel magneto-resistive (TMR) read-sensors. AMR read-sensors are taught without limitation by U.S. Pat. No. 5,005,096, entitled "Magnetoresistive Read Transducer Having Hard Magnetic Shunt Bias," which is hereby incorporated by reference in its entirety. AMR read-sensors may comprise other structures having similar functionality.

GMR read-sensors, which are also known as spin-valve read-sensors, are taught without limitation by U.S. Pat. No. 5,206,590, entitled "Magnetoresistive Sensor Based On The Spin Valve Effect," which is hereby incorporated by reference in its entirety. GMR read-sensors may comprise other structures having similar functionality. The GMR read-sensors typically have an internal antiparallel pinned layer for increased sensitivity, as taught without limitation by U.S. Pat. No. 5,465,185, entitled "Magnetoresistive Spin Valve Sensor With Improved Pinned Ferromagnetic Layer And Magnetic Recording System Using The Sensor," which is hereby incorporated by reference in its entirety.

Another form of read-sensor, TMR, uses a tunnel barrier layer to augment the GMR internal structure and to provide increased sensitivity, as taught without limitation by U.S. Pat. No. 5,764,567, entitled "Magnetic Tunnel Junction Device With Nonferromagnetic Interface Layer For Improved Magnetic Field Response," which is hereby incorporated by reference in its entirety. TMR read-sensors may comprise other structures having similar functionality.

In another embodiment, the scanner 107 may comprise magneto-resistive (MR) read-write heads for detecting micro-organisms and antigens that are attached to metal nanoparticles. An MR read-write head may scan a large number of biosamples deposited on a magnetic tape media as the MR read-write head traverses the tape media at a high speed. The tape drive electronics may then process the signals from the read-write MR head to detect the presence of target micro-organisms or antigens in the biosamples. Such a bio-assay process is described, for example, in the commonly-assigned US patent application entitled "Detection Of Analytes Via Nanoparticle-Labeled Substances With Electromagnetic Read-Write Heads", Ser. No. 12/888,388, herein incorporated by reference in its entirety.

The scanner 107 may be controlled by a controller 108 of the analytical system or data storage system 102. The controller 108 may read the signals, i.e., data and results, from the scanner 107 and converts the signals to digital for storage, for example, as data file 110. The data file 110 may be stored in a data storage subsystem 111 that is connected to the analytical system 102. The data files 110 may be in the form of image files or text files, e.g., TIFF, PDF files, and managed by the controller 108. In medical applications, the data files may be in the DICOM data format.

The controller 108 may further control the read/write component 106 which is in wireless communication with the wireless communication interface 105 to transfer data between the biosample plate 101 and the analytical system 102. In one embodiment, the controller 108 may be part of a control system in an electromagnetic tape drive that is used for scanning and analyzing the biosample 103.

Figure 2:
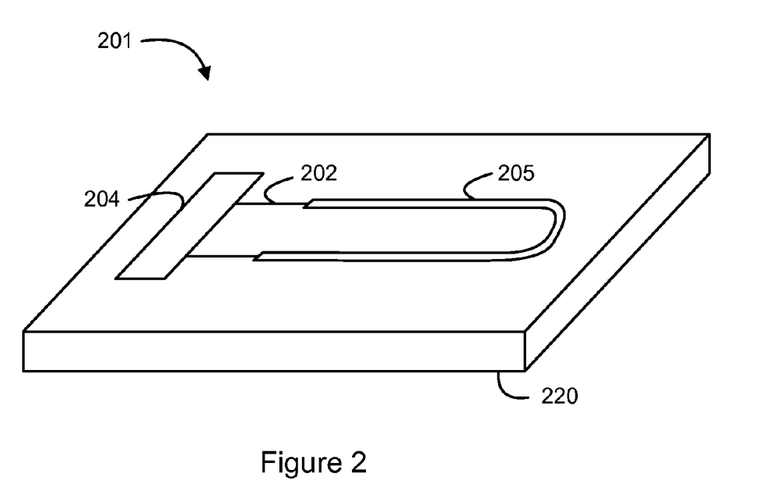
FIG. 2 illustrates a perspective view of an exemplary biosample plate with a memory component and a wireless communication interface for use with an analytical system or a data storage system, in accordance with an embodiment of the invention.

FIG. 2 illustrates a perspective view of an exemplary biosample plate with a data storage means and a wireless communication interface, according to an embodiment of the invention. Biosample plate 201 may comprise a base 220 that is made of, for example, glass, Pyrex™, or ceramic. The biosample plate 201 comprises a memory component 204 that may be a memory module attached to the base 220 or fabricated as part of the base 220. The memory component 204 may be an electrically-erasable programmable read-only memory (EEPROM), a phase-change memory, a flash memory, a NOR memory, or a NAND memory.

The biosample plate 201 includes a wireless communication interface 205 that is in electrical communication with the memory component 204 through connector 202 to allow data to be sent to and received from the memory component 204. In one embodiment, the wireless communication interface 205 is an antenna to allow data to be sent to and received from the biosample plate 201 in the form of radio signals.

Figure 3:
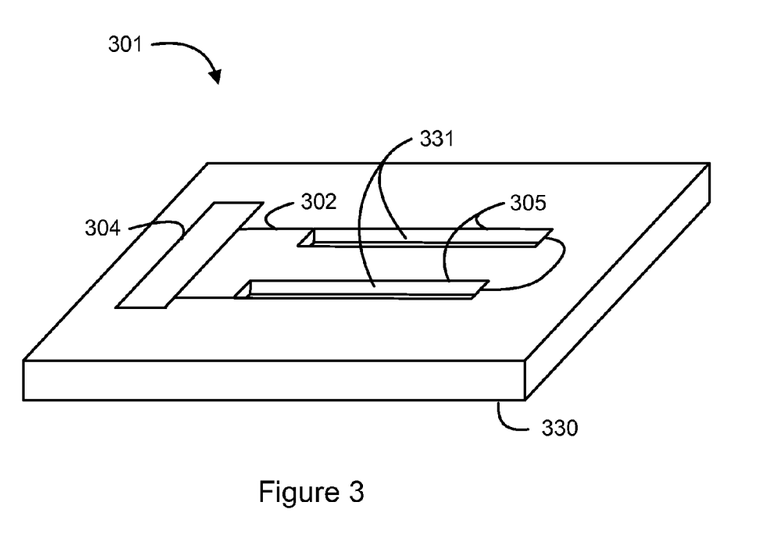
FIG. 3 illustrates a perspective view of an exemplary biosample plate with a memory component and a wireless communication interface formed from trenches in the plate, for use with an analytical system or a data storage system, in accordance with an embodiment of the invention.

FIG. 3 illustrates a perspective view of a biosample plate with a data storage means and a wireless communication interface, wherein the wireless communication interface comprises an antenna formed in the base of the biosample plate, according to an embodiment of the invention. The biosample plate 301 includes a base 330 which may be made of, for example, glass, Pyrex™, or ceramic. The base 330 receives a biosample 103 for analysis and includes a memory component 304 for storing information related to the biosample plate 301 and biosample 103, as described with reference to FIG. 2. The data stored in the memory component 304 may include information to uniquely identify the biosample plate and results from the analysis of the biosample 103. The base 330 further comprises a wireless communication interface 305 to provide the wireless transfer of information between the biosample plate 301 and a remote read/write or transceiver component 106. The remote read/write component 106 may be part of an analytical device or system 102, as described with reference to FIG. 1.

In the illustrated embodiment, the wireless communication interface 305 comprises one or more trenches 331 disposed in the base 330 wherein the bottom of trench 331 may be coated with a metallic material such as copper, silver, gold, or platinum. This metallic material acts as an antenna of the wireless communication interface 305 and further provides a medium for attaching biological specimens. The trench 331 may have a uniform width and depth to form side walls and end walls that have a uniform height. In one embodiment, the untrenched portion of base 330 may be coated with a diamond-like carbon material. The number of trenches, their shape, size and depth may vary depending on the particular design of the wireless communication interface 305. As an example, the wireless communication interface 305 may be a U-shape antenna that is disposed in trenches 331 in the base 330, as illustrated in FIG. 3. Trenches 331 may be used to contain biosamples captured by antibodies adhered to a metallic material, such as gold, at the bottom of trenches 331. Thus, the same metallic material serves two purposes, (a) it functions as the wireless communication interface 305 and (b) it anchors antibodies used to capture biological specimens such as cancer, viruses, bacteria, etc., for analysis. Wireless communication interface 305 is connected to memory component 304 by connector 302.

Figure 4:
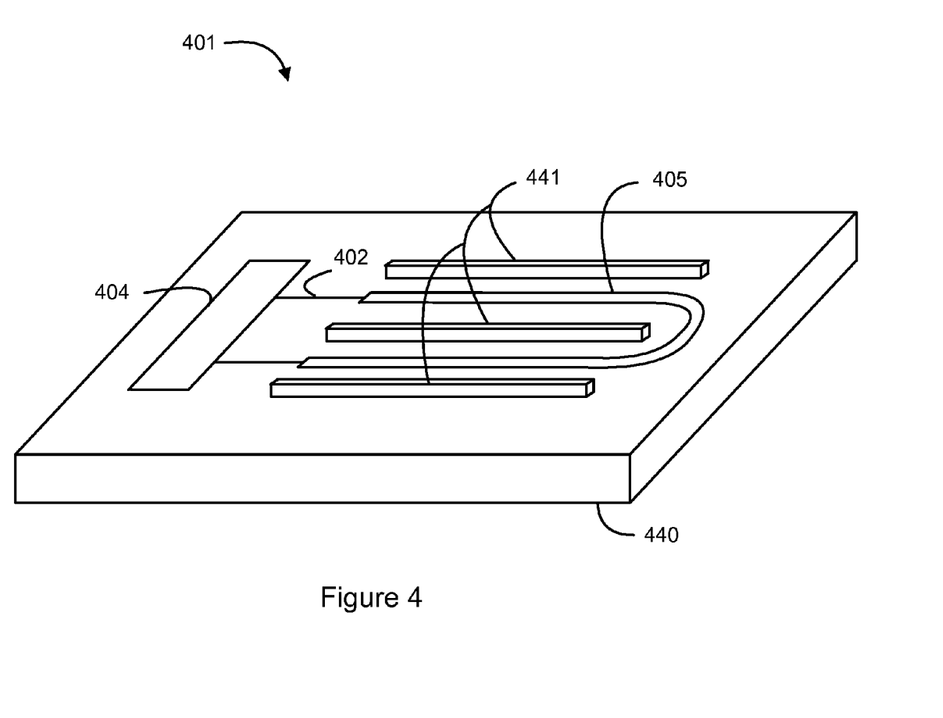
FIG. 4 illustrates a perspective view of an exemplary biosample plate with a memory component and a wireless communication interface that includes an antenna formed between parallel side walls on the plate, in accordance with an embodiment of the invention.

FIG. 4 illustrates a perspective view of an another exemplary embodiment of the wireless communication interface 105 in which the wireless communication interface is formed between parallel walls disposed on the base of a biosample plate. FIG. 4 illustrates three parallel side walls 441 disposed on the base 440 to form trenches between two adjacent side walls 441. An antenna 405 may be disposed in the trenches formed between the adjacent side walls 441 and acts as a wireless communication interface 405 for the biosamplate 401. The parallel side walls 441 may have uniform width and height. The antenna 405 is electrically connected to a memory component 404 by connector 402 to allow information in the memory component 404 to be sent to and received from a read/write or transceiver 106 by the antenna 405 through wireless transmission.

Figure 5:
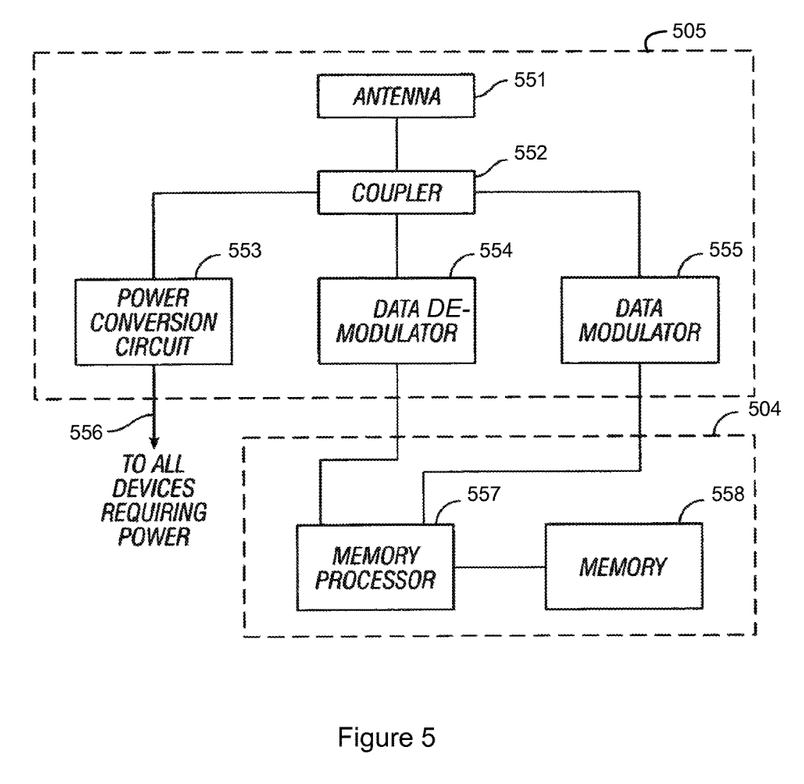
FIG. 5 illustrates a block diagram of the functional components of a memory component and a wireless communication interface for use with an analytical system or a data storage system, in accordance with an embodiment of the invention.

FIG. 5 illustrates a block diagram of the functional components of an embodiment of a memory component 504 and a wireless communication interface 505. In the illustrated embodiment, the wireless communication interface 505 is a radio frequency (RF) wireless interface. An example of an RF wireless interface is described in U.S. Pat. No. 4,941,201. A high frequency inductive wireless interface may also be employed, which is of sufficiently high frequency so that it does not adversely affect magnetic storage media that may be present in the analytical system 102. Examples of high frequency inductive wireless interfaces are described in U.S. Pat. No. 4,650,981, U.S. Pat. No. 4,758,836, and U.S. Pat. No. 3,859,624.

An antenna 551 may receive the RF signal from the RF interface of the analytical system 102, such as a data storage drive. A coupler 552 supplies the received signal to a power conversion circuit 553 and to a data demodulator 554. The power conversion circuit 553 converts the received signal to a power current, supplying the current on line 556 to all devices on the biosample plate 501, including the memory component 504, the data demodulator 554, and a data modulator 555. The received signal from antenna 551 may be encoded. The data demodulator 554 receives the incoming coded signal from coupler 552 and demodulates the signal to provide data signals to the memory component 504. Data signals from the memory component 504 are provided to the data modulator 555 which encodes the signals for transmission by coupler 552 and antenna 551 to the RF interface 106 of the analytical system 102.

The memory component 504 may comprise a memory processor 557, such as logic or a microprocessor chip, for example, an Intel Pentium™ chip arranged to operate in a low power environment, such as a portable computer, and an associated nonvolatile memory 558 that is also arranged to operate in a low power environment. The nonvolatile memory 558 may be an electrically-erasable programmable read-only memory (EEPROM), a phase-change memory, a flash memory, a NOR memory, or a NAND memory.

The memory processor 557 may have computer readable program code embodied therein, including suitable security and encryption/decryption algorithms, and the logic for accessing and operating the memory component 504. The memory component 504 may comprise a nonvolatile storage, as is known to those of skill in the art. The nonvolatile storage 558 may comprise a separate chip attached to the logic or memory processor 557, or may comprise a portion of the same chip. The computer readable program code may be stored in a nonvolatile internal memory of the processor 557 or in the nonvolatile memory 558, and loaded into the processor 557. Alternatively, the memory component 504 may be operated by a control system or processor of the analytical system 102 or an associated computer system.

Figure 6:
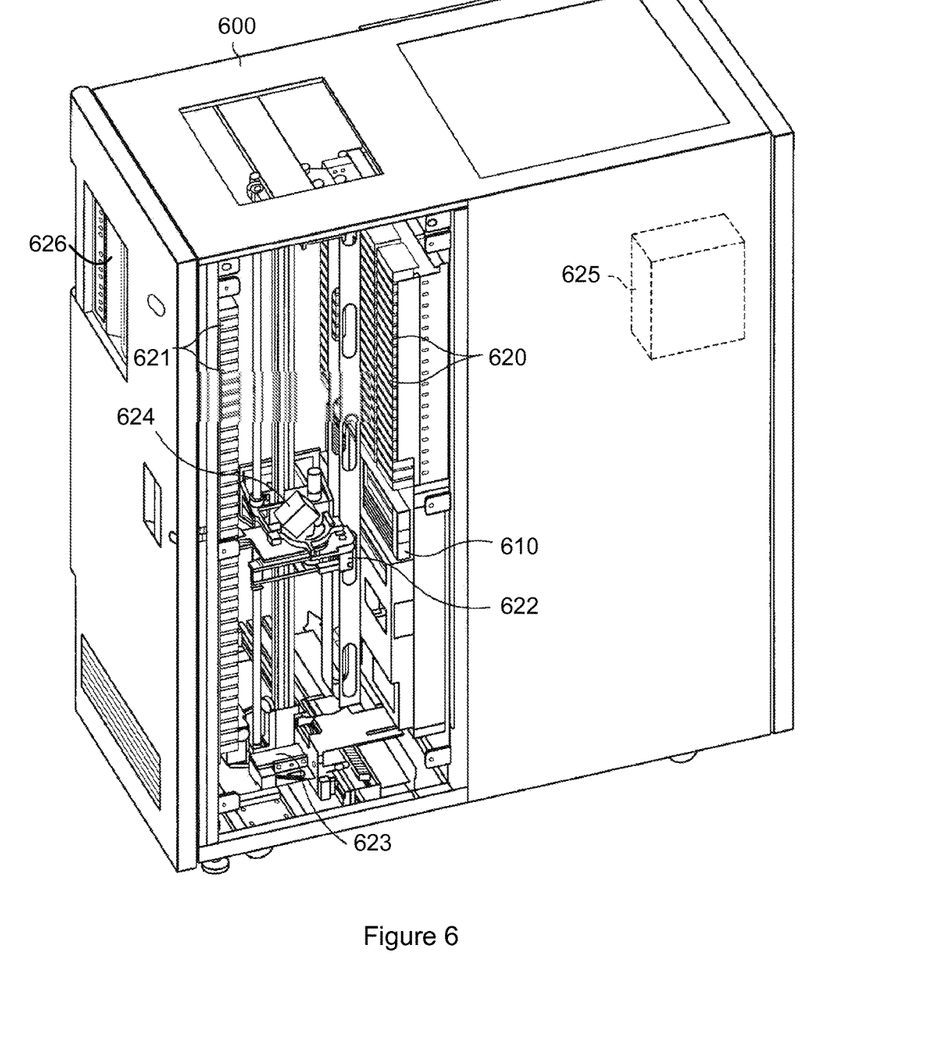
FIG. 6 illustrates a block diagram of the functional components in a data storage tape library that may be used for analyzing a biosample and storing biosample identification and analysis data, in accordance with an embodiment of the invention.

FIG. 6 illustrates an automated data storage tape library 600 that may be used for analyzing a biosample 103 and storing biosample identification and analysis data, in accordance with an embodiment of the invention. Biosamples 103 may be deposited on tape media, read and written by an MR head in the tape library 600, and analyzed by the tape library 600 in a bio-assay process.

The data storage tape library 600 is an automated tape library that may comprise multiple tape drives 610 for reading and writing on tape media, such as single-reel or two-reel magnetic tape cartridges. Examples of the library 600 include IBM TS3400™ and TS3500™ Tape Libraries, IBM TotalStorage™ 3494 Tape Libraries, and IBM 3952 ™ Tape Frames Model C20, which store magnetic tape cartridges and use IBM TS1130™ tape drives. Other examples of the library 600 include IBM TS3310™ and TS3100/ 3200™ tape libraries which store magnetic tape cartridges and use IBM LTO (Linear Tape Open) tape drives. Both the drives 610 and robotic picker 622 in the library 600 can record/read data on a biosample plate 101, provided that read/write component 106 and wireless communication interface 105 are both proximal and parallel to one another.

A plurality of tape media cartridges 620 are stored in banks or groups of storage slots 621. Tape media may encompass a variety of media, such as that contained in magnetic tape cartridges, magnetic tape cassettes, and optical tape cartridges, in various formats. For universal reference to any of these types of media, the terms "tape media" or "media" are used herein, and any of these types of containers are referred to as "tape cartridges" or "cartridges" herein. An access robot 623, including a cartridge picker 622 and a bar code reader 624 mounted on the picker 622, transports a selected cartridge 620 between a storage slot 621 and a drive 610.

The automated tape library 600 further has a library controller 625 which includes at least one microprocessor. The library controller 625 may serve to provide an inventory of the cartridges 620 and to control the library 600. Typically, the library controller 625 has suitable memory and data storage capability to control the operation of the library 600. The library controller 625 controls the actions of the access robot 623, cartridge picker 622, and bar code reader 624. The library controller 625 is interconnected through an interface to one or more host processors, which provides commands requesting access to particular tape media or to media in particular storage slots. A host, either directly, or through the library controller, controls the actions of the data storage drives 610. Commands for accessing data or locations on the tape media and information to be recorded on, or to be read from, selected tape media are transmitted between the drives 610 and the host. The library controller 625 is typically provided with a database for locating the tape cartridges 620 in the appropriate storage slots 621 and for maintaining the cartridge inventory.

Library 600 also includes an import/export mail slot 626, which is a portal allowing cartridges 620 to be entered into or removed from library 600. Since cartridges 620 have a generally identical exterior dimensions regardless of whether they hold data tape or biosample plates, cartridges 620 may enter library 600 through import/export mail slot 626, picked up by picker 622 and transported to either cartridge-storage slot 621 or drives 610. Drives 610 would have a common cartridge loader mechanism, whether the drive is a data drive or a bioanalysis drive, because of cartridges 620 having identical exterior dimensions. Similarly picker 622 may pick cartridge 620 from a drive 610 or cartridge-storage slot 621 and place it in import/export mail slot 626 for removal from library 600. In an alternate embodiment, biosample cartridges 620 are a different color from cartridges containing digital data, as well as containing information regarding their intended purpose in memories 732, FIG. 7.

Figure 7:
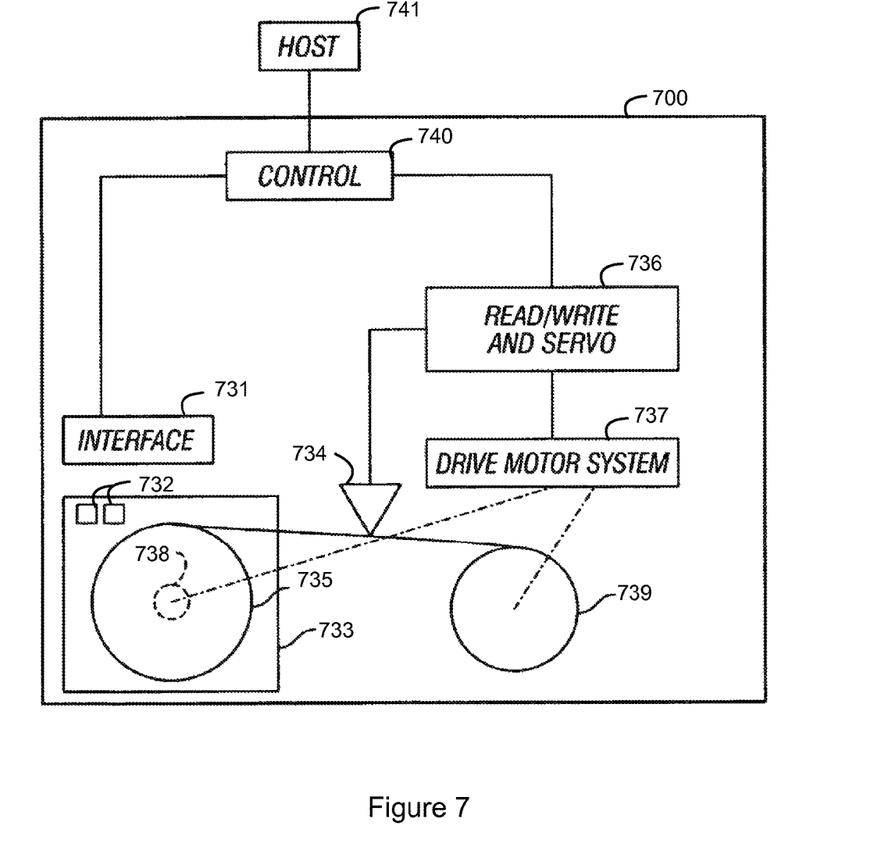
FIG. 7 illustrates a block diagram of the main functional components in a data storage tape drive that may be used for analyzing a biosample and storing biosample identification and analysis data, in accordance with an embodiment of the invention.

FIG. 7 illustrates a block diagram of the main functional components in a data storage tape drive 700, in accordance with an embodiment of the invention. The magnetic tape drive 700 comprises a memory interface 731 for reading information from and writing information to one or more of the cartridge memory 732 of the magnetic tape cartridge 733, for example, in a contactless manner.

A read/write system is provided for reading and writing information to the data storage media, such as magnetic tape, and may comprise a read/write head 734 with a servo system for moving the head laterally of the magnetic tape 735. The servo system may comprise a read/write and servo control 736 and a drive motor system 737 which moves the magnetic tape 735 between the cartridge reel 738 and the take up reel 739 and across the read/write head 734. The read/write and servo control 736 controls the operation of the drive motor system 737 to move the magnetic tape 735 across the read/write head 734 at a desired velocity. The read/write and servo control 736 may determine the location of the read/write head 734 with respect to the magnetic tape 735.

In one example, the read/write head 734 and read/write and servo control 736 employ servo signals on the magnetic tape 735 to determine the location of the read/write head 734, and in another example, the read/write and servo control 736 employs at least one of the reels, such as by means of a tachometer, to determine the location of the read/write head 734 with respect to the magnetic tape 735. The read/write head 734 and read/write and servo control 736 may comprise hardware elements and may comprise any suitable form of logic, including a processor operated by software, or microcode, or firmware, or may comprise hardware logic, or a combination.

A control system 740 communicates with the memory interface 731, and communicates with the read/write system, e.g., at read/write and servo control 736. The control system 740 may comprise any suitable form of logic, including a processor operated by software, or microcode, or firmware, or may comprise hardware logic, or a combination thereof. The control system 740 typically communicates with one or more host systems 741, and operates the data storage drive 700 in accordance with commands originating at a host. Alternatively, the data storage drive 700 may form part of a subsystem, such as a library, and may also receive and respond to commands from the subsystem.

As illustrated, the data storage drive 700 provides information to a cartridge memory 732 of the magnetic tape cartridge 733, and provides data to the magnetic tape 735 of the magnetic tape cartridge 733.

In one embodiment, the data storage tape drive 700 may function as an analytical system 102 for scanning the biosample plates 101 and analyzing biological samples 103 deposited on the biosample plates 101 to detect the presence of target antigens or substances. The magneto-resistive (MR) heads of the data storage drive 700 act as the scanners 107 for scanning the biosamples 103. For example, an MR read-write head may be used to detect micro-organisms and antigens that are attached to magnetized nanoparticles.

An MR read-write head may scan a large number of biosamples 103 deposited on a magnetic tape media as the MR read-write head traverses the tape media a high speed. The tape drive electronics may then process the signals from the read-write MR head to detect the presence of target micro-organisms or antigens in the biosamples 103.

Figure 8:
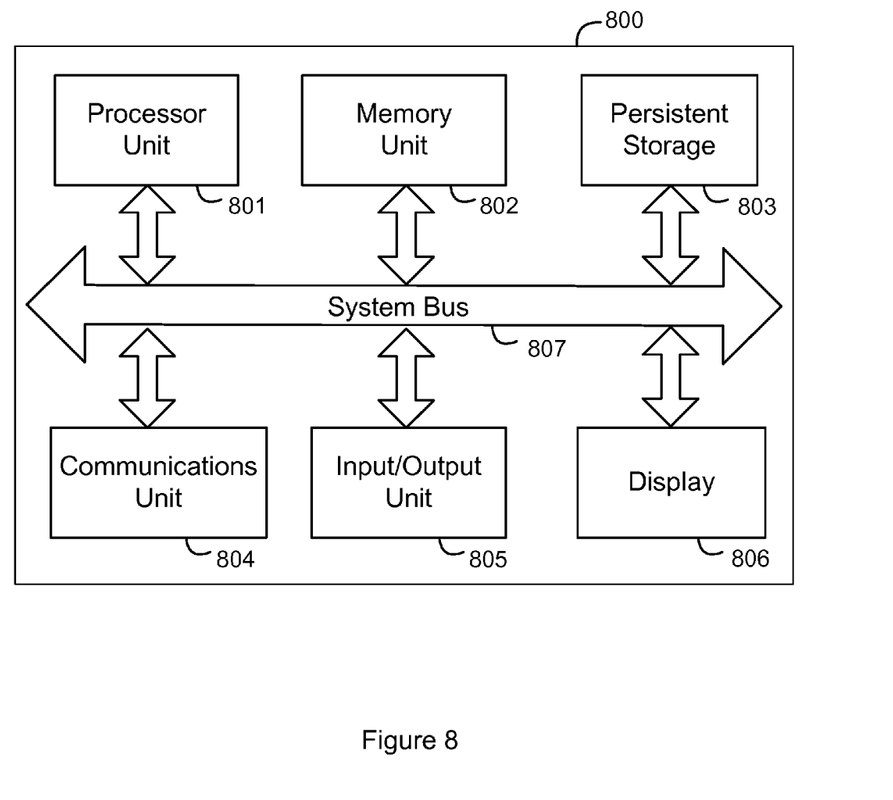
FIG. 8 illustrates a block diagram of the functional components in a computer, which may be part of a data storage tape library or a cartridge memory to provide control and processing functions, in accordance with an embodiment of the invention.

FIG. 8 illustrates a block diagram of a representative computer system, which may be incorporated in a data storage tape library and a cartridge memory to provide control and processing function, for providing aspects of the disclosure. Computer system 800 includes a processor 801, a memory 802, a persistent storage 803, a communication interface 804, an input/output unit 805, a display 806 and a system bus 807. Computer programs are typically stored in persistent storage 803 until they are needed for execution by an operating system running in memory 802. At that time, the programs are brought into the memory 802 so that they can be directly accessed by the processor 801. The processor 801 selects a part of memory 802 to read and/or write by using an address that the processor 801 gives to memory 802 along with a request to read and/or write. Usually, the reading and interpretation of an encoded instruction at an address causes the processor 801 to fetch a subsequent instruction, either at a subsequent address or some other address. The processor 801, memory 802, persistent storage 803, communication interface 804, input/output unit 805, and display 806 interface with each other through the system bus 807.

As will be appreciated by one skilled in the art, aspects of the present disclosure may be embodied as a method, system or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a wide area network (WAN), Ethernet, SCSI, iSCSI, Fibre Channel, Fibre Channel over Ethernet, and Infiniband, or the connection may be made to an external computer, for example, through the Internet using an Internet Service Provider.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures described above illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The subject matter described above is provided by way of illustration only and should not be construed as limiting. Various modifications and substitutions of the described components and operations can be made by those skilled in the art without departing from the spirit and scope of the present disclosure defined in the following claims, the scope of which is to be accorded the broadest interpretation so as to encompass such modifications and equivalent structures. As will be appreciated by those skilled in the art, the systems, methods, and procedures described herein can be embodied in a programmable computer, computer executable software, or digital circuitry. The software can be stored on computer readable media. For example, computer readable media can include a floppy disk, RAM, ROM, hard disk, removable media, flash memory, a "memory stick", optical media, magneto-optical media, CD-ROM, etc.

What is claimed is:

1. A biosample plate comprising:
a base for receiving a biosample;
a memory component coupled to the base for storing identification and analysis information related to the biosample; and
a wireless communication interface coupled to the memory component for transferring the information to and from the memory component,
wherein the wireless communication interface comprises a plurality of metal-coated trenches disposed in the base.

2. The biosample plate of claim 1, wherein the wireless communication interface further comprises an optical device.

3. The biosample plate of claim 2, wherein the optical device includes an optical laser.

4. The biosample plate of claim 1, wherein the memory component comprises a nonvolatile memory disposed on the base.

5. The biosample plate of claim 4, wherein the nonvolatile memory is selected from the group consisting of electrically-erasable programmable read-only memory (EEPROM), phase-change memory, flash memory, NOR memory, and NAND memory.

6. The biosample plate of claim 1, further comprising a plurality of parallel side walls disposed on the base to form the metal-coated trenches.

7. The biosample plate of claim 6, wherein the parallel side walls are characterized by a uniform width and a uniform height.

8. The biosample plate of claim 1, wherein the metal comprises platinum, and the biosample comprises antigens that are attached to the metal-coated trenches through antibodies.

9. The biosample plate of claim 1, wherein the wireless communication interface is provided in the form of a U-shape antenna disposed in the trenches.

10. The biosample plate of claim 9, wherein the antenna is electrically connected to the memory component by connector.

11. A system comprising the bio sample plate of claim 1, wherein the biosample plate is disposed on an electromagnetic tape media, wherein the wireless communication interface also uses magnetism for communication.

12. A biosample plate comprising:
a base for receiving a biosample;
a memory component coupled to the base for storing identification and analysis information related to the biosample; and
a wireless communication interface coupled to the memory component for transferring the information to and from the memory component;
wherein the wireless communication interface includes an optical device;
wherein the wireless communication interface uses radio signals for communication; and
wherein the wireless communication interface is formed by a plurality of metal-plated trenches disposed in the base.

13. The biosample plate of claim 12, further comprising a plurality of parallel side walls disposed on the base to form the metal-plated trenches.

14. The biosample plate of claim 12, wherein the metal is selected from the group consisting of gold, silver, copper and platinum, and the biosample comprises antigens that are attached to the metal-plated trenches through antibodies.

15. The biosample plate of claim 12, further comprising a plurality of parallel side walls disposed on the base to form the metal-plated trenches.

16. The biosample plate of claim 15, wherein the parallel side walls are characterized by a uniform width and a uniform height.

17. The biosample plate of claim 12, wherein the metal comprises platinum, and the biosample comprises antigens that are attached to the metal-plated trenches through antibodies.

18. The biosample plate of claim 12, wherein the wireless communication interface is provided in the form of a U-shape antenna disposed in the trenches.

19. The biosample plate of claim 18, wherein the antenna is electrically connected to the memory component by connector.

* * * * *